United States Patent
Park et al.

(10) Patent No.: US 11,600,847 B2
(45) Date of Patent: Mar. 7, 2023

(54) LITHIUM SECONDARY BATTERY

(71) Applicant: SK On Co., Ltd., Seoul (KR)

(72) Inventors: Dai In Park, Daejeon (KR); Hyo Shin Kwak, Daejeon (KR); Myoung Lae Kim, Daejeon (KR); In Haeng Cho, Daejeon (KR)

(73) Assignee: SK On Co., Ltd., Seoul (KR)

( * ) Notice: Subject to any disclaimer, the term of this patent is extended or adjusted under 35 U.S.C. 154(b) by 284 days.

(21) Appl. No.: 16/526,013

(22) Filed: Jul. 30, 2019

(65) Prior Publication Data
US 2020/0044279 A1 Feb. 6, 2020

(30) Foreign Application Priority Data
Aug. 2, 2018 (KR) .................. 10-2018-0090381

(51) Int. Cl.
| | |
|---|---|
| *H01M 10/0525* | (2010.01) |
| *H01M 10/0567* | (2010.01) |
| *H01M 10/0569* | (2010.01) |
| *H01M 4/38* | (2006.01) |
| *H01M 4/134* | (2010.01) |
| *H01M 4/133* | (2010.01) |
| *H01M 4/583* | (2010.01) |
| *C07C 11/02* | (2006.01) |
| *H01M 4/02* | (2006.01) |

(52) U.S. Cl.
CPC ......... *H01M 10/0525* (2013.01); *C07C 11/02* (2013.01); *H01M 4/133* (2013.01); *H01M 4/134* (2013.01); *H01M 4/386* (2013.01); *H01M 4/583* (2013.01); *H01M 10/0567* (2013.01); *H01M 10/0569* (2013.01); *H01M 2004/027* (2013.01); *H01M 2300/0028* (2013.01)

(58) Field of Classification Search
CPC ...... H01M 4/131; H01M 4/134; H01M 4/139; H01M 4/606; H01M 10/0525; H01M 10/0567; H01M 10/0589; H01M 2004/027; H01M 4/133; H01M 4/386; C07C 11/02; C07C 11/12
See application file for complete search history.

(56) References Cited

U.S. PATENT DOCUMENTS

| | | | |
|---|---|---|---|
| 5,879,834 A | 3/1999 | Mao | |
| 6,291,107 B1 * | 9/2001 | Shimizu | H01M 10/0525 429/324 |
| 2008/0014496 A1 * | 1/2008 | Watanabe | H01M 50/572 429/129 |
| 2011/0136019 A1 * | 6/2011 | Amiruddin | H01M 10/0525 429/332 |
| 2016/0099481 A1 * | 4/2016 | Akagawa | H01M 10/446 429/185 |
| 2017/0345581 A1 † | 11/2017 | Kim | |

FOREIGN PATENT DOCUMENTS

| | | |
|---|---|---|
| JP | 3163078 B2 | 5/2001 |
| JP | 2010044883 A | 2/2010 |
| KR | 20180023567 A1 † | 3/2018 |
| WO | 2013047067 A1 † | 4/2013 |

\* cited by examiner
† cited by third party

*Primary Examiner* — Amanda C. Walke
(74) *Attorney, Agent, or Firm* — The Webb Law Firm

(57) ABSTRACT

Provided is a lithium secondary battery including an anode including a silicon-based anode active material; a cathode; and an electrolyte, the electrolyte including a lithium salt, a non-aqueous organic solvent, and a conjugated diene compound.

11 Claims, No Drawings

LITHIUM SECONDARY BATTERY

CROSS-REFERENCE TO RELATED APPLICATION

This application claims priority to Korean Patent Application No. 10-2018-0090381 filed Aug. 2, 2018, the disclosure of which is hereby incorporated by reference in its entirety.

TECHNICAL FIELD

The following disclosure relates to a lithium secondary battery.

BACKGROUND

Recently, as portable electronic devices have been widely popularized and have been becoming smaller, thinner, and lighter, research has been actively carried out to make a secondary battery used as a power source thereof, wherein the secondary battery has a small size and a lightweight and is capable of charging and discharging for a long time.

The lithium secondary battery generates electrical energy by oxidation and reduction reactions when lithium ions are intercalated into and deintercalated from a cathode and an anode, uses materials capable of intercalating and deintercalating lithium ions as the anode and the cathode, and is manufactured by charging an organic electrolyte or a polymer electrolyte between the cathode and the anode.

Currently widely used organic electrolytes include, for example, ethylene carbonate, propylene carbonate, dimethoxyethane, gamma butyrolactone, N,N-dimethylformamide, tetrahydrofuran, or acetonitrile. However, these organic electrolytes are generally volatile and are highly flammable, so when these are applied to a lithium ion secondary battery, there is a problem in safety at a high temperature, such as causing an ignition by internal short-circuit during internal heating due to overcharging and overdischarging.

In addition, the lithium secondary battery is intercalated into carbon by moving lithium ions released from the lithium metal oxide, which is a cathode, to a carbon electrode, which is an anode, during initial charging. In this case, since the lithium ions are highly reactive, the lithium ions react with the surface of the carbon particle, which is the anode active material, and electrolyte to form a coating, called a solid electrolyte interface (SEI) film, on the surface of the anode.

The performance of the lithium secondary battery largely depends on the constitution of the organic electrolyte, and the SEI film formed by the reaction between the organic electrolyte and the electrode.

That is, the formed SEI film suppresses side reactions between carbon materials and electrolyte solvents, for example, decomposition of the electrolyte on the surface of the carbon particle, which is an anode; prevents collapse of anode materials or the like due to co-intercalation of the electrolyte solvents into the anode materials; and minimizes performance deterioration of the battery by faithfully performing its role as a conventional lithium ion tunnel.

Thus, in order to solve the problems as described above, various attempts have been made to develop a new organic electrolyte including additives.

As an example, U.S. Pat. No. 5,879,834 also discloses a method for improving the safety of a battery by adding a small amount of an aromatic compound such as biphenyl and 3-chlorothiophene and electrochemically polymerizing under abnormal overvoltage conditions to increase internal resistance. However, when an additive such as biphenyl is used, biphenyl or the like is gradually decomposed during a charging and discharging process when a relatively high voltage is generated locally under a normal drive voltage, or the amount of biphenyl or the like gradually decreases when the battery is discharged at a high temperature for a long period of time. As a result, there is a problem that safety may not be guaranteed, a problem in the storage characteristics or the like, after 300 cycles of charging and discharging.

Meanwhile, a carbon-based anode active material has been mainly used as an anode active material of the lithium secondary battery. Examples of such carbon-based anode active material include crystalline carbons such as graphite and artificial graphite, and amorphous carbons such as soft carbon and hard carbon. Of crystalline carbons, graphite is particularly representative.

However, since the upper limit of the theoretical capacity of a carbon-based anode active material such as graphite is limited, application to a high capacity lithium secondary battery is limited. Thus, in order to overcome this limitation, various materials, for example, metals or semimetals, such as silicon (Si), tin (Sn), aluminum (Al), germanium (Ge), lead (Pb) and zinc (Zn) have been studied as anode active materials.

Silicon has been particularly prominent as a high-capacity anode material because it has a higher theoretical capacity (4200 mAh/g for $Li_{4.4}Si$) and a relatively lower reduction potential (0 to 0.4 vs. Li/Li) than graphite (theoretical capacity 372 mAh/g), which is a carbon material.

However, the silicon-based anode active material has poor lifespan characteristics and has a limitation in commercialization. In the anode including such silicon-based anode active material, lithium is intercalated/deintercalated by repetitive charging and discharging, resulting in serious volume expansion (300% or more) and shrinkage of the active material particles. As a result, a new surface is continuously exposed to the electrolyte due to the cracking of silicon, thereby continuously consuming a large amount of lithium ion source, and generating a thick and unstable coating at the interface between silicon and an electrolyte. Such an unstable coating may hinder high-temperature thermal stability as well as electrochemical performance of a silicon anode such as lifespan characteristics. Thus, research has been attempted to modify the surface of the anode.

Recently, it has been reported that the thermal stability of a silicon anode is improved by introducing vinylene carbonate (VC) and fluoroethylene carbonate (FEC) as an additive into an electrolyte of 1.3 M $LiPF_6$ in EC/DEC (3/7) to produce stable SEI. However, in the case of FEC, continuous decomposition occurs during charging and discharging, which makes it difficult to use for a long period of time.

Thus, there is a continuing need for research to improve the lifespan characteristics and the stability at a high temperature while maintaining a high capacity retention rate of the lithium secondary battery using the silicon-based anode active material.

SUMMARY

An embodiment of the present invention is directed to providing a lithium secondary battery having excellent high-temperature storage characteristics while maintaining good basic performances such as high-efficiency charging and discharging characteristics and lifespan characteristics.

In one general aspect, a lithium secondary battery includes an anode including a silicon-based anode active material; a cathode; and an electrolyte, wherein the electrolyte includes a lithium salt, a non-aqueous organic solvent, and a conjugated diene compound represented by the following Formula 1:

[Formula 1]

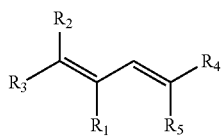

wherein $R_1$ is hydrogen or $C_1$-$C_3$alkyl substituted with a $C_4$-$C_8$alkenyl, when $R_1$ is hydrogen, $R_2$, $R_3$, $R_4$, and $R_5$ are each independently $C_1$-$C_3$alkyl, and when $R_1$ is $C_1$-$C_3$alkyl substituted with a $C_4$-$C_8$ alkenyl, $R_2$, $R_3$, $R_4$, and $R_5$ are all hydrogen.

The conjugated diene compound may be represented by the following Formula 2 or Formula 3:

[Formula 2]

[Formula 3]

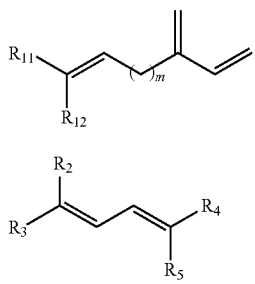

wherein m is an integer of 1 to 3;

$R_{11}$ and $R_{12}$ are each independently $C_1$-$C_3$alkyl; and $R_2$, $R_3$, $R_4$, and $R_5$ are each independently $C_1$-$C_3$alkyl.

The conjugated diene compound may be a conjugated diene compound selected from the following structural formulas:

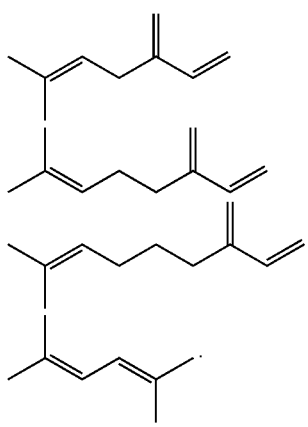

The conjugated diene compound may be included in an amount of 0.1 to 15.0% by weight, based on the total weight of the electrolyte.

The electrolyte may further include one or two or more additives selected from the group consisting of an oxalato phosphate-based compound, an oxalato borate-based compound, a fluorine-substituted carbonate-based compound, a vinylidene carbonate-based compound, and a sulfinyl group-containing compound.

The electrolyte may further include additives selected from the group consisting of lithium tetrafluoro(oxalato)phosphate (LiTFOP), lithium difluoro bis(oxalato)phosphate (LiDFOP), lithium difluoro(oxalato)borate (LiDFOB), lithium bis(oxalato)borate (LiB($C_2O_4$)$_2$, LiBOB), fluoroethylene carbonate (FEC), vinylene carbonate (VC), vinyl ethylene carbonate (VEC), divinyl sulfone, ethylene sulfite, propylene sulfite, diallyl sulfonate, ethane sultone, propane sultone (PS), butane sultone, ethene sultone, butene sultone, and propene sultone (PRS).

The additive may be included in an amount of 0.1 to 5.0% by weight, based on the total weight of the electrolyte.

The non-aqueous organic solvent may be selected from a cyclic carbonate-based solvent, a linear carbonate-based solvent, and a mixed solvent thereof. The cyclic carbonate may be selected from the group consisting of ethylene carbonate, propylene carbonate, butylene carbonate, vinylene carbonate, vinyl ethylene carbonate, fluoroethylene carbonate, and a mixture thereof, and the linear carbonate may be selected from the group consisting of dimethyl carbonate, diethyl carbonate, dipropyl carbonate, ethyl methyl carbonate, methyl propyl carbonate, methyl isopropyl carbonate, ethyl propyl carbonate, and a mixture thereof.

The non-aqueous organic solvent may have a mixing volume ratio of the linear carbonate-based solvent: the cyclic carbonate-based solvent of 1:1 to 9:1.

The lithium salt may be one or two or more selected from the group consisting of $LiPF_6$, $LiBF_4$, $LiClO_4$, $LiSbF_6$, $LiAsF_6$, $LiN(SO_2C_2F_5)_2$, $LiN(CF_3SO_2)_2$, $LiN(SO_3C_2F_5)$ 2, $LiN(SO_2F)$ 2, $LiCF_3SO_3$, $LiC_4F_9SO_3$, $LiC_6HsSO_3$, LiSCN, $LiAlO_2$, $LiAlCl_4$, $LiN(C_xF_{2x+1}SO_2)(C_yF_{2y+1}SO_2)$ (where x and y are each independently natural number), LiCl, LiI, and $LiB(C_2O_4)_2$.

The lithium salt may be present in a concentration of 0.1 to 2.0 M.

The silicon-based anode active material may be selected from Si, $SiO_x$ (0<x<2), Si—Z alloy (where Z is an alkali metal, an alkaline earth metal, a Group 13 element, a Group 14 element, a Group 15 element, a Group 16 element, a transition metal, a rare earth element, or a combination element thereof, and is not Si), and a combination thereof.

The anode may further include a carbon-based anode active material.

DETAILED DESCRIPTION OF EMBODIMENTS

Hereinafter, the present invention will be described in more detail. Technical terms and scientific terms used herein have the general meaning understood by those skilled in the art to which the present invention pertains, unless otherwise defined, and a description for the known function and configuration unnecessarily obscuring the gist of the present invention will be omitted in the following description.

The term "alkyl" used herein includes both linear and branched forms.

The term "alkylalkenyl" used herein refers to an alkenyl substituted with one or more alkyls.

The term "discharging" used herein refers to a process in which lithium ions are deintercalated from an anode, and the term "charging" used herein refers to a process in which lithium ions are intercalated into an anode.

Hereinafter, a lithium secondary battery according to an embodiment of the present invention will be described in detail.

The present invention relates to a lithium secondary battery having excellent high-temperature storage characteristics and lifespan characteristics. The lithium secondary battery of the present invention includes an anode including a silicon-based anode active material; a cathode; and an electrolyte, the electrolyte including a lithium salt, a non-aqueous organic solvent, and a conjugated diene compound represented by the following Formula 1:

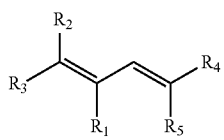

[Formula 1]

wherein $R_1$ is hydrogen or $C_1$-$C_3$alkyl substituted with a $C_4$-$C_8$ alkenyl, when $R_1$ is hydrogen, $R_2$, $R_3$, $R_4$, and $R_5$ are each independently $C_1$-$C_3$alkyl, and when $R_1$ is $C_1$-$C_3$alkyl substituted with a $C_4$-$C_8$ alkenyl, $R_2$, $R_3$, $R_4$, and $R_5$ are all hydrogen.

The conjugated diene compound of Formula 1 included in the electrolyte of the lithium secondary battery of the present invention forms a solid electrolyte interface (SEI) of a polymer structure in which a new double bond is formed at carbon atoms 2 and 3 while 1,4-polymerization is generated during reduction decomposition in a pre-charge region. The SEI thus formed contains a large amount of carbon-carbon double bonds (C=C bonds), such that the SEI has elasticity, whereby cracking of SEI may be suppressed during shrinkage/expansion. That is, the SEI formed on the surface of the silicon-based anode by the electrolyte reduction reaction during a first charging process is thermally stable. Therefore, direct contact between the silicon-based anode and the electrolyte may be prevented, thereby suppressing side reactions between lithium ions stored in the silicon-based anode and the electrolyte at a high temperature, and the SEI cracking due to shrinkage/expansion of silicon-based anode during charging and discharging may also be suppressed due to elasticity of the SEI, thereby improving the lifespan. The conjugated diene compound is thus more effective as an electrolyte additive for a lithium secondary battery including a silicon-based anode having a large volume expansion during charging and discharging.

That is, the conjugated diene compound may effectively form a thermally stable and elastic SEI on the surface of a silicon-based anode. Thus, the SEI cracking phenomenon may be suppressed during the volume expansion/shrinkage caused by charging and discharging of the silicon-based anode, thereby significantly improving the lifespan characteristics, and inhibiting the decomposition reaction between the anode and the electrolyte at a high temperature. Therefore, the lithium secondary battery employing the electrolyte including the conjugated diene compound according to the present invention has excellent high-temperature storage characteristics, but also mitigates deterioration of the fully-lithiated silicon-based anode, thereby maximizing thermal stability at a high temperature.

In addition, the lithium secondary battery of the present invention suppresses the SEI cracking in the secondary battery employing the silicon-based anode due to the conjugated diene compound included in the employed electrolyte, thereby significantly improving the lifespan characteristics, even if the content of FEC which is mainly used is significantly reduced or FEC is replaced.

The conjugated diene compound according to an embodiment of the present invention may preferably be represented by the following Formula 2 or Formula 3 in terms of chemical stability and electrical characteristics:

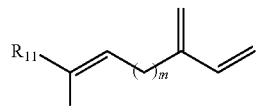

[Formula 2]

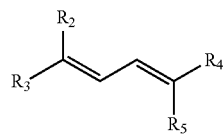

[Formula 3]

wherein m is an integer of 1 to 3;

$R_{11}$ and $R_{12}$ are each independently $C_1$-$C_3$alkyl; and $R_2$, $R_3$, $R_4$, and $R_5$ are each independently $C_1$-$C_3$alkyl.

The conjugated diene compound according to an embodiment of the present invention may be selected from the following structural formulas, but present invention is not limited thereto:

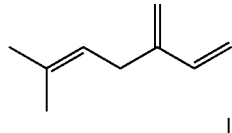 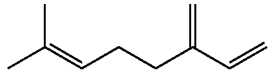

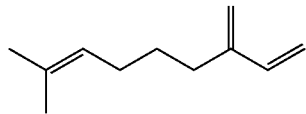 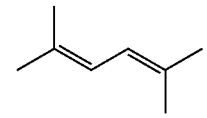

In an embodiment of the present invention, in order to further improve high-temperature storage characteristics and lifespan characteristics, in the conjugated diene compound of Formula 1, when $R_1$ is alkylalkenyl, $R_1$ may have a total of 5 to 9 carbons, and more preferably 5 to 7 carbons.

In an embodiment of the present invention, in the conjugated diene compound of Formula 2, preferably, $R_{11}$ and $R_{12}$ may be identical to each other, m may be an integer of 1 to 3, more preferably, $R_{11}$ and $R_{12}$ may both be methyl, still more preferably, $R_{11}$ and $R_{12}$ may both be methyl, and m may be an integer of 2, in terms of chemical stability and electrical characteristics.

In an embodiment of the present invention, the conjugated diene compound of Formula 3, preferably, $R_2$, $R_3$, $R_4$, and $R_5$ may be identical to each other, and more preferably, $R_2$, $R_3$, $R_4$, and $R_5$ may all be methyl, in terms of chemical stability and electrical characteristics.

In an embodiment of the present invention, the conjugated diene compound of Formula 1 may be included in an amount of 0.1 to 10.0% by weight, based on the total weight of the electrolyte, in terms of improving high-temperature stability and the capacity retention rate, and preventing deterioration of the characteristics of the lithium secondary battery due to rapid deterioration of the lifespan or the like. The conjugated diene compound of Formula 1 may be included in an amount of 0.5 to 5.0% by weight, and more preferably 0.5 to 3.0% by weight, based on the total weight of the electrolyte, in terms of improving high-temperature storage characteristics and lifespan characteristics.

In an embodiment of the present invention, the electrolyte may further include one or two or more known additives selected from the group consisting of an oxalato phosphate-based additive, an oxalato borate-based compound, a fluorine-substituted carbonate-based compound, a vinylidene carbonate-based compound, and a sulfinyl group-containing compound, as additives for improving the lifespan and high-temperature storage stability of the battery by suppressing gas generated by the decomposition reaction with the electrolyte solvent on the surface of the cathode after being coordinated on the surface of the cathode.

The oxalato borate-based compound may be a compound represented by the following Formula 4 or lithium bis(oxalato)borate ($LiB(C_2O_4)_2$, LiBOB):

[Formula 4]

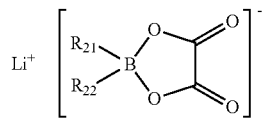

wherein $R_{21}$ and $R_{22}$ are each independently halogen or halo $C_1$-$C_{10}$alkyl.

Specific examples of the oxalato borate-based additive include $LiB(C_2O_4)F_2$ (lithium difluoro(oxalato)borate, LiDFOB) or $LiB(C_2O_4)_2$ (lithium bis(oxalato)borate, LiBOB).

The oxalato phosphate-based additive may be a compound represented by the following Formula 5 or lithium difluoro bis(oxalato)phosphate (LiDFOP):

[Formula 5]

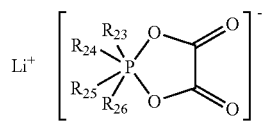

wherein $R_{23}$ to $R_{26}$ are each independently halogen or halo $C_1$-$C_{10}$alkyl.

Specific examples of the oxalatophosphate-based additive include lithium tetrafluoro(oxalato)phosphate (LiTFOP) or lithium difluoro bis(oxalato)phosphate (LiDFOP).

The fluorine-substituted carbonate-based compound may be fluoroethylene carbonate (FEC), difluoroethylene carbonate (DFEC), fluorodimethyl carbonate (FDMC), fluoroethylmethyl carbonate (FEMC), or a combination thereof.

The vinylidene carbonate-based compound may be vinylene carbonate (VC), vinyl ethylene carbonate (VEC), or a mixture thereof.

The sulfinyl group (S=O)-containing compound may be sulfone, sulfite, sulfonate, or sultone (cyclic sulfonate), which may be used alone or in an admixture thereof. Specifically, the sulfone may be represented by the following Formula 6, and may be divinyl sulfone. The sulfite may be represented by the following Formula 7, and may be ethylene sulfite or propylene sulfite. The sulfonate may be represented by the following Formula 8, and may be diallyl sulfonate. In addition, non-limiting examples of the sultone include ethane sultone, propane sultone, butane sultone, ethene sultone, butene sultone, propene sultone or the like.

[Formula 6]

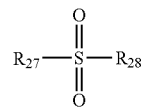

[Formula 7]

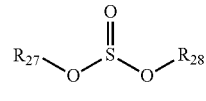

[Formula 8]

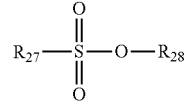

wherein $R_{27}$ and $R_{28}$ are each independently hydrogen, halogen, $C_1$-$C_{10}$alkyl, $C_2$-$C_{10}$alkenyl, halo $C_1$-$C_{10}$alkyl, or halo $C_2$-$C_{10}$alkenyl.

In an embodiment of the present invention, the electrolyte preferably may further include one or two or more additives selected from the group consisting of lithium tetrafluoro(oxalato)phosphate (LiTFOP), lithium difluoro bis(oxalato)phosphate (LiDFOP), lithium difluoro(oxalato)borate (LiDFOB), lithium bis(oxalato)borate (LiBOB), fluoroethylene carbonate (FEC), vinylene carbonate (VC), vinyl ethylene carbonate (VEC), divinyl sulfone, ethylene sulfite, propylene sulfite, diallyl sulfonate, ethane sultone, propane sultone, butane sultone, ethene sultone, butene sultone, and propene sultone. The electrolyte more preferably may further include one or two or more additives selected from the group consisting of lithium tetrafluoro(oxalato)phosphate (LiTFOP), lithium difluoro bis(oxalato)phosphate (LiDFOP), lithium bis(oxalato)borate (LiBOB), vinylene carbonate (VC), vinyl ethylene carbonate (VEC), ethylene sulfite, ethane sultone, and propane sultone.

The electrolyte according to an embodiment of the present invention still more preferably may further include lithium difluoro bis(oxalato)phosphate (LiDFOP), lithium bis(oxalato)borate (LiBOB), or a mixture thereof as an additional additive, and a lithium secondary battery including a mixture of lithium difluoro bis(oxalato)phosphate (LiDFOP) and lithium bis(oxalato)borate (LiBOB) is more preferable in terms of having improved properties than the lithium secondary battery including each of them.

In an embodiment of the present invention, the content of the additive is not particularly limited, but may be included in an amount of 0.1 to 5.0% by weight, and more preferably 0.1 to 3% by weight in the electrolyte of the secondary battery, based on the total weight of the electrolyte, in order to improve the battery lifespan. When the additive is included within the content range as described above, the lifespan characteristics and high-temperature storage characteristics of the battery may be improved by effectively suppressing gas generated by the decomposition reaction with the electrolyte solvent on the surface of the cathode after being coordinated on the surface of the cathode.

In an embodiment of the present invention, the non-aqueous organic solvent may include carbonate, ester, ether, or ketone alone, or a mixed solvent thereof. The non-aqueous organic solvent is preferably selected from a cyclic carbonate-based solvent, a linear carbonate-based solvent, and a mixed solvent thereof, and is most preferably a mixture of a cyclic carbonate-based solvent and a linear carbonate-based solvent. The cyclic carbonate-based solvent has a high polarity, which may sufficiently dissociate lithium ions, but has a disadvantage in that the ion conductivity is low due to a high viscosity. Therefore, the characteristics of the lithium secondary battery may be optimized by using a mixed solvent of the cyclic carbonate-based solvent and a linear carbonate-based solvent having a low polarity but a low viscosity.

The cyclic carbonate-based solvent may be selected from the group consisting of ethylene carbonate, propylene carbonate, butylene carbonate, vinylene carbonate, vinylethylene carbonate, fluoroethylene carbonate, and a mixture thereof. The linear carbonate-based solvent may be selected from the group consisting of dimethyl carbonate, diethyl carbonate, dipropyl carbonate, ethyl methyl carbonate, methyl propyl carbonate, methyl isopropyl carbonate, ethyl propyl carbonate, and a mixture thereof.

In an embodiment of the present invention, the non-aqueous organic solvent is a mixed solvent of the cyclic carbonate-based solvent and the linear carbonate-based solvent, and is used by mixing the linear carbonate solvent: the cyclic carbonate solvent in a volume ratio of 1:1 to 9:1, and preferably 1.5:1 to 4:1.

In an embodiment of the present invention, the lithium salt may be, but is not limited thereto, one or two or more selected from the group consisting of $LiPF_6$, $LiBF_4$, $LiClO_4$, $LiSbF_6$, $LiAsF_6$, $LiN(SO_2C_2F_5)_2$, $LiN(CF_3SO_2)_2$, $LiN(SO_3C_2F_5)_2$, $LiN(SO_2F)_2$, $LiCF_3SO_3$, $LiC_4F_9SO_3$, $LiC_6HsSO_3$, $LiSCN$, $LiAlO_2$, $LiAlCl_4$, $LiN(C_xF_{2x+1}SO_2)(C_yF_{2y+1}SO_2)$ (where x and y are each independently natural number), $LiCl$, $LiI$, and $LiB(C_2O_4)_2$.

The concentration of the lithium salt is used preferably in the range of 0.1 to 2.0 M, more preferably in the range of 0.7 to 1.6 M. When the concentration of the lithium salt is less than 0.1 M, the conductivity of the electrolyte decreases, thereby deteriorating performance of the electrolyte. When the concentration of the lithium salt exceeds 2.0 M, the viscosity of the electrolyte increases, thereby decreasing mobility of the lithium ion. The lithium salt serves as a source of the lithium ion in the battery, thereby enabling operation of a basic lithium secondary battery.

The electrolyte according to an embodiment of the present invention may improve a conserved property of a lithium secondary battery including a silicon-based anode, and may significantly improve high-temperature stability and lifespan characteristics.

The electrolyte according to an embodiment of the present invention is generally stable in a temperature range of −20° C. to 80° C., and may be applied to a secondary battery operating at middle and high voltage in the range of 2.8V to 4.6V to improve cell performance and stability. For example, the electrolyte may be useful for a high-voltage battery operating in a voltage range of 4.3V to 4.6V, and thus may be applied to all lithium secondary batteries such as a lithium ion battery and a lithium polymer battery.

Non-limiting examples of the lithium secondary battery according to an embodiment of the present invention include a lithium metal secondary battery, a lithium ion secondary battery, a lithium polymer secondary battery, or a lithium ion polymer secondary battery.

The lithium secondary battery according to an embodiment of the present invention has excellent high-temperature characteristics and excellent stability while maintaining good basic performances such as high-efficiency charging and discharging characteristics and lifespan characteristics.

The anode includes an anode current collector and an anode active material layer formed on the anode current collector, the anode active material layer includes an anode active material, and the anode active material includes a silicon-based anode active material. The conjugated diene compound represented by Formula 1 included in the electrolyte may suppress the reaction between the silicon-based anode active material and the electrolyte, thereby improving battery performance.

According to an embodiment of the present invention, a high capacity of lithium secondary battery having a theoretical capacity of 4400 mAh/g may be implemented due to the silicon-based anode active material, and is not particularly limited as long as it is generally used in the art. The silicon-based anode active material may include, for example, a material selected from Si, $SiO_x$ (0<x<2), Si—Z alloy (where Z is an alkali metal, an alkaline earth metal, a Group 13 element, a Group 14 element, a Group 15 element, a Group 16 element, a transition metal, a rare earth element, or a combination element thereof, and Si is excluded in Z), and a combination thereof. The element Z may be selected from the group consisting of Mg, Ca, Sr, Ba, Ra, Sc, Y, La, Ti, Zr, Hf, V, Nb, Ta, Cr, Mo, W, Tc, Re, Fe, Ru, Os, Co, Rh, Ir, Ni, Pd, Pt, Cu, Ag, Au, Zn, Cd, B, Ge, P, As, Sb, Bi, S, Se, Te, Po, and a combination thereof. In addition, such a silicon-based anode active material such as Si, SiOx, or Si—Z alloy may include substantially crystalline (including single crystal, polycrystal), amorphous, or a mixed form thereof.

The silicon-based anode active material may be used alone or in combination of two or more.

The anode may further include a compound generally used as an anode active material in a lithium battery. That is, the anode active material layer may further include other general anode active materials in addition the silicon-based anode active material.

The general anode active material as described above may be used without limitation as long as it is commonly used in the art. For example, as the anode active material, a material capable of reversibly intercalating/deintercalating lithium ions, a lithium metal, a metal capable of alloying with lithium, a material capable of doping and dedoping lithium, or a transition metal oxide may be used, and of these, two or more of them in a mixed or combined form may also be used.

The material capable of reversibly intercalating/deintercalating lithium ions as described above is carbon-based material, and any carbon-based anode active material generally used in lithium batteries may be used. Representative examples thereof include crystalline carbon, amorphous carbon, or a mixture thereof. Non-limiting examples of the amorphous carbon include soft carbon (low-temperature sintered carbon), hard carbon, coke, mesocarbon microbead (MCMB) calcined at 1500° C. or less, mesophase pitch-based carbon fiber (MPCF) or the like. Non-limiting examples of the crystalline carbon include graphite such as natural graphite, artificial graphite, and expanded graphite, graphene, fullerene soot, carbon nanotube, carbon fiber or the like. The carbon-based anode active material may be used in spherical, plate, fibrous, tubular or powder form.

Examples of a metal capable of alloying with lithium include aluminum, zinc, bismuth, cadmium, antimony, silicon, lead, tin, gallium or indium.

Examples of the material capable of doping and dedoping lithium include Sn, $SnO_2$, Sn—Y alloy (where Y is an element selected from the group consisting of an alkali metal, an alkaline earth metal, Group 13 to 16 elements, a transition metal, a rare earth element, and a combination thereof, and is not Sn) or the like. The element Y may be selected from the group consisting of Mg, Ca, Sr, Ba, Ra, Sc, Y, Ti, Zr, Hf, Rf, V, Nb, Ta, Db, Cr, Mo, W, Sg, Tc, Re, Bh, Fe, Pb, Ru, Os, Hs, Rh, Ir, Pd, Pt, Cu, Ag, Au, Zn, Cd, B, Al, Ga, Sn, In, Ti, Ge, P, As, Sb, Bi, S, Se, Te, Po, and a combination thereof.

Examples of the transition metal oxide include vanadium oxide, lithium vanadium oxide or the like.

According to an embodiment of the present invention, the anode may include a mixture of a silicon-based anode active material and a carbon-based anode active material.

The anode active material according to an embodiment of the present invention may preferably be a mixture of the silicon-based anode active material and the carbon-based anode active material at a weight ratio of 5:95 to 50:50, and more preferably, silicon oxide and graphite at a weight ratio of 5:95 to 50:50.

The cathode includes a cathode current collector and a cathode active material layer formed on the cathode current collector.

The cathode active material layer includes a cathode active material capable of intercalating and deintercalating lithium ions, such cathode active material is a lithium-containing metal oxide, and any of those usually used in the art may be used without limitation. Examples of the cathode active material are preferably a composite metal oxide of lithium and a metal selected from cobalt, manganese, nickel, and a combination thereof.

Specific examples of the cathode active material include compounds represented by any one of the following Formulas: $Li_aA_{1-b}B_bD_2$ (where $0.90 \leq a \leq 1.8$, $0 \leq b \leq 0.5$); $Li_aE_{1-b}B_bO_{2-c}D_c$ (where $0.90 \leq a \leq 1.8$, $0 \leq b \leq 0.5$, $0 \leq c \leq 0.05$); $LiE_{2-b}B_bO_{4-c}D_c$ (where $0 \leq b \leq 0.5$, $0 \leq c \leq 0.05$); $Li_aNi_{1-b-c}Co_bB_cD_\alpha$ (where $0.90 \leq a \leq 1.8$, $0 \leq b \leq 0.5$, $0 \leq c \leq 0.05$, $0 \leq \alpha \leq 2$); $Li_aNi_{1-b-c}Co_bB_cO_{2-\alpha}F_\alpha$ (where $0.90 \leq a \leq 1.8$, $0 \leq b \leq 0.5$, $0 \leq c \leq 0.05$, $0 < \alpha < 2$); $Li_aNi_{1-b-c}Co_bB_cO_{2-\alpha}F_2$ (where $0.90 \leq a \leq 1.8$, $0 \leq b \leq 0.5$, $0 \leq c \leq 0.05$, $0 < \alpha < 2$); $Li_aNi_{1-b-c}Mn_bB_cD_\alpha$ (where $0.90 \leq a \leq 1.8$, $0 \leq b \leq 0.5$, $0 \leq c \leq 0.05$, $0 < \alpha \leq 2$); $Li_aNi_{1-b-c}Mn_bB_cO_{2-\alpha}F_\alpha$ (where $0.90 \leq a \leq 1.8$, $0 \leq b \leq 0.5$, $\leq c \leq 0.05$, $0 \leq \alpha \leq 2$); $Li_aNi_{1-b-c}Mn_bB_cO_{2-\alpha}F_2$ (where $0.90 \leq a \leq 1.8$, $0 \leq b \leq 0.5$, $0 \leq c \leq 0.05$, $0 < \alpha < 2$); $Li_aNi_bE_cG_dO_2$ (where $0.90 \leq a \leq 1.8$, $0 \leq b \leq 0.9$, $0 \leq c \leq 0.5$, $0.001 \leq d \leq 0.1$); $Li_aNi_bCo_cMn_dGeO_2$ (where $0.90 \leq a \leq 1.8$, $0 \leq b \leq 0.9$, $0 \leq c \leq 0.5$, $0 \leq d \leq 0.5$, $0.001 \leq e \leq 0.1$); $Li_aNiG_bO_2$ (where $0.90 \leq a \leq 1.8$, $0.001 \leq b \leq 0.1$); $Li_aCoG_bO_2$ (where $0.90 \leq a \leq 1.8$, $0.001 \leq b \leq 0.1$); $Li_aMnG_bO_2$ (where $0.90 \leq a \leq 1.8$, $0.001 \leq b \leq 0.1$); $Li_aMn_2GbO_4$ (where $0.90 \leq a \leq 1.8$, $0.001 \leq b \leq 0.1$); $QO_2$; $QS_2$; $LiQS_2$; $V_2O_5$; $LiV_2O_5$; $LiIO_2$; $LiNiVO_4$; $Li_{(3-f)}J_2(PO_4)_3(0 \leq f \leq 2)$; $Li_{(3-f)}Fe_2(PO_4)_3(0 \leq f \leq 2)$; and $LiFePO_4$.

In the Formulas, A may be Ni, Co, Mn, or a combination thereof; B may be Al, Ni, Co, Mn, Cr, Fe, Mg, Sr, V, a rare earth element, or a combination thereof; D may be O, F, S, P, or a combination thereof; E may be Co, Mn, or a combination thereof; F may be F, S, P, or a combination thereof; G may be Al, Cr, Mn, Fe, Mg, La, Ce, Sr, V, or a combination thereof; Q may be Ti, Mo, Mn, or a combination thereof; I may be Cr, V, Fe, Sc, Y, or a combination thereof; and J may be V, Cr, Mn, Co, Ni, Cu, or a combination thereof. Examples thereof include $LiCoO_2$, $LiMn_xO_{2X}$ (x=1, 2), $LiNi_{1-x}Mn_xO_{2X}$ ($0<x<1$), $LiNi_{1-x-y}Co_xMn_yO_2$ ($0 \leq x \leq 0.5$, $0 \leq y \leq 0.5$), $FePO_4$ or the like.

The cathode or anode may be manufactured by dispersing an electrode active material, a binder, and a conductive material, and if necessary, a thickener in a solvent to prepare an electrode slurry composition, and applying the slurry composition to an electrode current collector. As the cathode current collector, aluminum or an aluminum alloy may be commonly used, and as the anode current collector, copper or a copper alloy may be commonly used. The cathode current collector and the anode current collector may be in the form of a foil or a mesh.

A binder is a material which serves as a paste of the active material, mutual adhesion of the active material, adhesion to the current collector, and buffering effect on expansion and contraction of the active material or the like. For example, the binder includes polyvinylidene fluoride (PVdF), a copolymer of polyhexafluoropropylene-polyvinylidene fluoride (PVdF/HFP), poly(vinyl acetate), polyvinyl alcohol, polyethylene oxide, polyvinyl pyrrolidone, alkylated polyethylene oxide, polyvinyl ether, poly(methyl methacrylate), poly(ethyl acrylate), polytetrafluoroethylene, polyvinyl chloride, polyacrylonitrile, polyvinylpyridine, styrene-butadiene rubber, acrylonitrile-butadiene rubber or the like. The content of the binder is 0.1 to 30% by weight, and preferably 1 to 10% by weight, based on the electrode active material. When the content of the binder is excessively small, adhesion between the electrode active material and the current collector is insufficient. Meanwhile, when the content of the binder is excessively large, adhesion is improved but the content of the electrode active material is reduced accordingly, which is disadvantageous for increasing the battery capacity.

A conductive material is used for imparting conductivity to the electrode, and may be any material as long as it is an electro conductive material without causing any chemical change in the battery constituted. Examples thereof include at least one selected from the group consisting of a graphite-based conductive material, a carbon black-based conductive material, and a metal-based or metal compound-based conductive material. Examples of the graphite-based conductive material include artificial graphite, natural graphite or the like. Examples of the carbon black-based conductive material include acetylene black, ketjen black, denkablack, thermal black, channel black or the like. Examples of the metal-based or metal compound-based conductive material include peroskite materials such as tin, tin oxide, tin phosphate ($SnPO_4$), titanium oxide, potassium titanate, $LaSrCoO_3$, or $LaSrMnO_3$. However, the conductive material is not limited to the materials as listed above.

The content of the conductive material is preferably 0.1 to 10% by weight, based on the electrode active material. When the content of the conductive material is less than 0.1% by weight, based on the electrode active material, electrochemical characteristics are deteriorated, and when the content of the conductive material exceeds 10% by weight, based on the electrode active material, an energy density per weight is decreased.

The thickener is not particularly limited as long as it controls the viscosity of an active material slurry. Examples thereof include carboxymethyl cellulose, hydroxymethyl cellulose, hydroxyethyl cellulose, hydroxypropyl cellulose or the like.

As the solvent in which the electrode active material, the binder, the conductive material or the like is dispersed, a non-aqueous solvent or an aqueous solvent is used. Examples of the non-aqueous solvent include N-methyl-2-pyrrolidone (NMP), dimethylformamide, dimethylacetamide, N,N-dimethylaminopropylamine, ethylene oxide, tetrahydrofuran or the like.

The lithium secondary battery of the present invention may include a separator which prevents a short-circuit between the cathode and the anode and provides a passage for the lithium ion. As such separator, a polyolefin-based polymer membrane such as polypropylene, polyethylene, polyethylene/polypropylene, polyethylene/polypropylene/polyethylene, and polypropylene/polyethylene/polypropylene, or a multi-membrane thereof, a microporous film, woven fabrics, or nonwoven fabrics may be used. In addition, a film coated with a resin having excellent stability may be used for a porous polyolefin film.

A coating depending on the use of the electrolyte may be formed on the anode interface of the lithium secondary battery. The anode coating is an SEI layer having improved stability which does not cause modification during high-temperature storage and may maintain a solid state even after charging and discharging for a long period of time.

The lithium secondary battery of the present invention may be other shapes such as a cylindrical shape, a pouch shape or the like in addition to the square shape. The secondary battery is also suitable for applications requiring high voltage, high output, and high temperature driving such as an electric vehicle in addition to the use of conventional mobile phones, portable computers or the like. In addition, the secondary battery may be used in a hybrid vehicle or the like by being coupled to a conventional internal combustion engine, a fuel battery, a super capacitor or the like, and may be used for electric bicycles, power tools and all other applications requiring high output, high voltage, and high temperature driving.

Hereinafter, Inventive Example and Comparative Examples will be described. However, the following Examples are only a preferred embodiment of the present invention, and the present invention is not limited to the following Examples. It is assumed that the lithium salt is all dissociated so that the concentration of the lithium ion is 1 mol (1M), and a basic electrolyte may be formed by dissolving a corresponding amount of the lithium salt such as $LiPF_6$ in a basic solvent so that the lithium salt is a concentration of 1 mol (1M).

[Examples 1 to 12 and Comparative Examples 1 to 7]Manufacture of Lithium Secondary Battery An electrolyte was prepared by dissolving $LiPF_6$ in a mixed solvent of ethylene carbonate (EC):ethyl methyl carbonate (EMC):diethyl carbonate (DEC) having the volume ratio of 25:45:30 so as to have a 1.0 M solution, as a basic electrolyte (1.0 M $LiPF_6$, EC/EMC/DEC=25/45/30), and further adding components shown in the following Table 1.

A battery to which the non-aqueous electrolyte is applied was manufactured as follows.

$LiNi_{0.6}Co_{0.2}Mn_{0.2}O_2$ as a cathode active material, polyvinylidene fluoride (PVdF) as a binder, and carbon as a conductive material were mixed at a weight ratio of 92:4:4, and then dispersed in N-methyl-2-pyrrolidone to prepare a cathode slurry. The slurry was applied on an aluminum foil having a thickness of 20 μm, and then dried and rolled to manufacture a cathode.

Artificial graphite, natural graphite, and silicon oxide as an anode active material were mixed at a weight ratio of 60:25:15, respectively. The anode active material, styrene-butadiene rubber (SBR) as a binder, and carboxymethyl cellulose (CMC) as a thickener were mixed at a weight ratio of 96:2:2, respectively, and then dispersed in water to prepare an anode slurry. The slurry was applied on a copper foil having a thickness of 15 μm, and then dried and rolled to manufacture an anode.

A cell was configured by stacking a film separator made of polyethylene (PE) and having a thickness of 25 μm between the electrodes thus manufactured, and using a pouch having a size of thickness 5 mm×width 50 mm×length 60 mm, and the non-aqueous electrolyte was injected thereto, thereby manufacturing a 1.8 Ah-class lithium secondary battery.

Performance of the 1.8 Ah-class battery thus manufactured was evaluated as follows, and the results are shown in Table 2 below. Evaluation factors were as follows:

*Evaluation Factors*

1. Formation capacity: After charging/discharging at 0.5 C was performed twice, discharge capacity of the battery was measured at 0.5 C.

2. Measurement of direct current internal resistance (DCIR) at room temperature: The resistance was measured by using an end-voltage value obtained by charging the battery at a current of 0.5 C up to 60% of state of charge (SOC) at room temperature and performing charging and discharging at a current of 0.2 C, 0.5 C, 1 C, 1.5 C, 2 C, 2.5 C, and 3 C for 10 seconds, as a slope value of the linear plot.

3. Storage at 60° C. high temperature: The battery was charged with CC CV (4.2V, 0.05 C cut-off) at 1 C rate at room temperature, and stored in a 60° C. oven for 6 weeks at a high temperature.

1) Thickness increase rate: The battery was taken out from the oven. A thickness of the center in the hot state was measured by a thickness gauge, and the thickness increase rate (%) of the battery was calculated.

Thickness increase rate (%) of the battery=[(final thickness−initial thickness)/initial thickness]×100(%)

2) Capacity retention rate: After the battery was allowed to stand at room temperature for 30 minutes to measure IR, the capacity retention rate was calculated as a percentage by dividing the capacity of the battery after CC discharging at 1 C rate (2.7V cut-off) by the capacity measured before storage.

Capacity retention rate (%) of the battery=(final capacity/initial capacity)×100(%)

4. Lifespan at room temperature: The battery was charged with CC-CV (4.2V, 0.05 C cut-off) at 1 C rate at room temperature, and then repeatedly discharged 300 times at a current of 1 C rate to 2.7V. Here, the $1^{st}$ discharging capacity was denoted by C, and the $300^{th}$ discharge capacity was divided by the $1^{st}$ discharge capacity to calculate the capacity retention rate during the lifespan.

TABLE 1

| Example | Composition of electrolyte (100 wt. % in total) |
|---|---|
| Example 1 | Basic electrolyte + conjugated diene compound (1) 0.5 wt. % |
| Example 2 | Basic electrolyte + conjugated diene compound (1) 1.0 wt. % |
| Example 3 | Basic electrolyte + conjugated diene compound (1) 2.0 wt. % |
| Example 4 | Basic electrolyte + conjugated diene compound (1) 0.5 wt. % + LiDFOP 1.0 wt. % |
| Example 5 | Basic electrolyte + conjugated diene compound (1) 0.5 wt. % + LiBOB 1.0 wt. % |
| Example 6 | Basic electrolyte + conjugated diene compound (1) 0.5 wt. % + LiDFOP 1.0 wt. % + LiBOB 1.0 wt. % |
| Example 7 | Basic electrolyte + conjugated diene compound (2) 0.5 wt. % |
| Example 8 | Basic electrolyte + conjugated diene compound (2) 1.0 wt. % |
| Example 9 | Basic electrolyte + conjugated diene compound (2) 2.0 wt. % |
| Example 10 | Basic electrolyte + conjugated diene compound (2) 0.5 wt. % + LiDFOP 1.0 wt. % |

TABLE 1-continued

| Example | Composition of electrolyte (100 wt. % in total) |
|---|---|
| Example 11 | Basic electrolyte + conjugated diene compound (2) 0.5 wt. % + LiBOB 1.0 wt. % |
| Example 12 | Basic electrolyte + conjugated diene compound (2) 0.5 wt. % + LiDFOP 1.0 wt. % + LiBOB 1.0 wt. % |
| Comparative Example 1 | Basic electrolyte |
| Comparative Example 2 | Basic electrolyte + FEC 1 wt. % |
| Comparative Example 3 | Basic electrolyte + Isoprene 0.5 wt. % |
| Comparative Example 4 | Basic electrolyte + β-Ionone 0.5 wt. % |
| Comparative Example 5 | Basic electrolyte + FEC 1.0 wt. % + LiDFOP 1.0 wt. % |
| Comparative Example 6 | Basic electrolyte + FEC 1.0 wt. % + LiBOB 1.0 wt. % |
| Comparative Example 7 | Basic electrolyte + FEC 1.0 wt. % + LiDFOP 1.0 wt. % + LiBOB 1.0 wt. % |

Basic electrolyte: 1M $LiPF_6$, EC/EMC/DEC = 25/45/30
Conjugated diene compound (1):

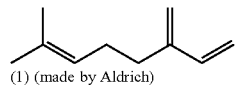

(1) (made by Aldrich)
Conjugated diene compound (2):

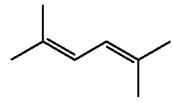

(2) (made by Aldrich)
LiDFOP: Lithium difluoro bis(oxalato)phosphate
LiBOB: Lithium bis(oxalato)borate
FEC: Fluoroethylene carbonate

TABLE 2

| Lithium secondary battery | Room temperature | | After 42 days at 60° C. | | Capacity retention rate (%) during lifespan |
|---|---|---|---|---|---|
| | Initial capacity (mAh) | Initial internal resistance (mΩ) | Capacity retention rate (%) | Thickness increase rate (%) | |
| Example 1 | 1810 | 47.0 | 63% | 99% | 54% |
| Example 2 | 1792 | 49.7 | 71% | 84% | 55% |
| Example 3 | 1761 | 52.9 | 71% | 80% | 51% |
| Example 4 | 1820 | 48.4 | 72% | 58% | 74% |
| Example 5 | 1819 | 49.1 | 70% | 72% | 70% |
| Example 6 | 1822 | 47.6 | 77% | 41% | 86% |
| Example 7 | 1790 | 50.9 | 60% | 99% | 50% |
| Example 8 | 1760 | 52.8 | 67% | 91% | 53% |
| Example 9 | 1714 | 53.5 | 67% | 84% | 49% |
| Example 10 | 1790 | 50.9 | 68% | 79% | 70% |
| Example 11 | 1760 | 50.8 | 67% | 91% | 64% |
| Example 12 | 1813 | 48.1 | 75% | 68% | 79% |
| Comparative Example 1 | 1821 | 45.7 | 41% | 143% | 24% |
| Comparative Example 2 | 1826 | 46.5 | 64% | 128% | 60% |
| Comparative Example 3 | 1785 | 52.9 | 54% | 110% | 34% |
| Comparative Example 4 | 1787 | 52.4 | 51% | 115% | 31% |
| Comparative Example 5 | 1822 | 47.4 | 67% | 105% | 60% |
| Comparative Example 6 | 1821 | 47.6 | 64% | 110% | 54% |
| Comparative Example 7 | 1825 | 47.2 | 70% | 101% | 65% |

As shown in Table 2, it could be appreciated that a lithium secondary battery employing an electrolyte including conjugated diene compounds 1 or 2 as a specific additive had excellent cycle life characteristics at room temperature, exhibited a higher capacity recovery rate than the batteries of Comparative Examples 1 to 7 even after the battery was allowed to stand at 60° C. for 42 days, and exhibited a very low thickness increase rate, thereby obtaining very high high-temperature stability. Meanwhile, it could be appreciated that batteries of Comparative Examples 1 to 7 had low lifespan characteristics and very high thickness increase rates, thereby deteriorating the high-temperature stability.

In particular, it could be appreciated that the battery of Comparative Example 2 employing an electrolyte including FEC, which is a conventional silicon-based anode additive, as an electrolyte additive, had a high thickness increase rate at a high temperature, thereby deteriorating the high-temperature stability. In addition, it could be appreciated that the batteries of Comparative Examples 3 and 4 employing electrolyte including isoprene and β-ionone, which are known as a carbon-based anode additive, had low lifespan characteristics, and had low capacity recovery rates and high thickness increase rates at a high temperature, thereby remarkably deteriorating the high temperature stability.

From this, it could be appreciated that the lithium secondary battery employing the electrolyte containing the conjugated diene compound 1 or 2 as the specific additive of the present invention significantly improves the high-temperature stability and the lifespan characteristics. In addition, the electrolyte of the present invention further includes lithium difluoro bis(oxalato)phosphate (LiDFOP), lithium bis(oxalato)borate (LiBOB), or a mixture thereof as an additional additive to further improve the high-temperature storage stability and the lifespan characteristics. Thus, the lithium secondary battery including the secondary battery electrolyte of the present invention has very high efficiency, stability, and lifespan characteristics.

In particular, the lithium secondary battery employing the electrolyte including both the conjugated diene compound 1 or 2 as the specific additive of the present invention and both of LiDFOP and LiBOB as the additional additives has improved lifespan characteristics and high temperature stability.

That is, the lithium secondary battery of the present invention exhibits significantly improved lifespan characteristics and excellent high-temperature characteristics while maintaining good basic performances such as high-efficiency charging and discharging characteristics due to the electrolyte including the conjugated diene compound of Formula 1 or 2 as a specific additive which is decomposed on the surface of the silicon-based anode before the lithium salt and the non-aqueous organic solvent to form the SEI coating more stably and efficiently.

The lithium secondary battery of the present invention exhibits significantly improved lifespan characteristics and excellent high-temperature characteristics while maintaining good basic performances such as high-efficiency charging and discharging characteristics due to the electrolyte including the conjugated diene compound of Formula 1 which is decomposed on the surface of the anode, in particular, on the surface of the silicon-based anode before the lithium salt and the non-aqueous organic solvent to form the SEI coating more stably and efficiently.

As described above, while the present invention has been described in detail with respect to exemplary embodiments thereof, it will be appreciated by those skilled in the art that various changes can be made therein without departing from the spirit and scope of the invention as defined by the appended claims. Therefore, further modifications in the embodiments of the present invention will not deviate from the technology of the present invention.

What is claimed is:

1. A lithium secondary battery comprising:
an anode including a silicon-based anode active material; a cathode; and an electrolyte,
wherein the electrolyte consists of at least one lithium salt, at least one non-aqueous organic solvent, at least one conjugated diene compound selected from the following structural formulae:

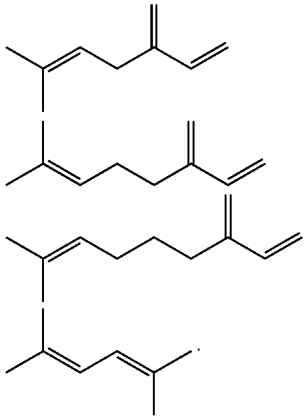

and one or more additives selected from an oxalato phosphate-based compound or an oxalato borate-based compound.

2. The lithium secondary battery of claim 1, wherein the at least one conjugated diene compound is included in an amount of 0.1 to 10% by weight, based on the total weight of the electrolyte.

3. The lithium secondary battery of claim 1, wherein the additive(s) are selected from lithium tetrafluoro(oxalato)phosphate, lithium difluoro bis(oxalato)phosphate, lithium difluoro(oxalato)borate or lithium bis(oxalato)borate.

4. The lithium secondary battery of claim 1, wherein the additives are included in an amount of 0.1 to 5.0% by weight, based on the total weight of the electrolyte.

5. The lithium secondary battery of claim 1, wherein the at least one non-aqueous organic solvent is selected from a cyclic carbonate-based solvent, a linear carbonate-based solvent, and a mixed solvent thereof.

6. The lithium secondary battery of claim 5, wherein the cyclic carbonate-based solvent is selected from the group consisting of ethylene carbonate, propylene carbonate, butylene carbonate, vinylene carbonate, vinyl ethylene carbonate, fluoroethylene carbonate, and a mixture thereof, and the linear carbonate-based solvent is selected from the group consisting of dimethyl carbonate, diethyl carbonate, dipropyl carbonate, ethyl methyl carbonate, methyl propyl carbonate, methyl isopropyl carbonate, ethyl propyl carbonate, and a mixture thereof.

7. The lithium secondary battery of claim 5, wherein the non-aqueous organic solvent has a mixing volume ratio of the linear carbonate-based solvent:the cyclic carbonate-based solvent of 1:1 to 9:1.

8. The lithium secondary battery of claim 1, wherein the at least one lithium salt is one or two or more selected from the group consisting of $LiPF_6$, $LiBF_4$, $LiClO_4$, $LiSbF_6$, $LiAsF_6$, $LiN(SO_2C_2F_5)_2$, $LiN(CF_3SO_2)_2$, $LiN(SO_3C_2F_5)_2$, $LiN(SO_2F)_2$, $LiCF_3SO_3$, $LiC_4F_9SO_3$, $LiC_6H_5SO_3$, LiSCN, $LiAlO_2$, $LiAlCl_4$, $LiN(C_xF_{2x+1}SO_2)(C_yF_{2y+1}SO_2)$, where x and y are each independently natural number, LiCl, LiI, and $LiB(C_2O_4)_2$.

9. The lithium secondary battery of claim 1, wherein the at least one lithium salt is present in a concentration of 0.1 to 2.0 M.

10. The lithium secondary battery of claim 1, wherein the silicon-based anode active material is selected from Si, $SiO_x(0<x<2)$, Si—Z, and a combination thereof: wherein Z is an alkali metal, an alkaline earth metal, a Group 13 element, a Group 14 element, a Group 15 element, a Group 16 element, a transition metal, a rare earth element, or a combination element thereof, and is not Si.

11. The lithium secondary battery of claim 10, wherein the anode further includes a carbon-based anode active material.

* * * * *